(12) United States Patent
Boese et al.

(10) Patent No.: US 8,634,620 B2
(45) Date of Patent: Jan. 21, 2014

(54) METHOD FOR SUPPLYING A 3D X-RAY IMAGE DATA RECORD FOR A MOVING OBJECT WITH HIGHLY ABSORBENT MATERIAL

(75) Inventors: Jan Boese, Eckental (DE); Günter Lauritsch, Nürnberg (DE); Christopher Rohkohl, Bochum (DE); Bernhard Scholz, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 97 days.

(21) Appl. No.: 13/456,480

(22) Filed: Apr. 26, 2012

(65) Prior Publication Data

US 2012/0275656 A1 Nov. 1, 2012

(30) Foreign Application Priority Data

Apr. 28, 2011 (DE) .......................... 10 2011 017 710

(51) Int. Cl.
G06K 9/00 (2006.01)
(52) U.S. Cl.
USPC .......................................................... 382/128
(58) Field of Classification Search
USPC .................. 382/128–134; 128/920–925; 356/39–49; 600/407–414, 424–426; 345/581–618; 250/455
See application file for complete search history.

(56) References Cited

FOREIGN PATENT DOCUMENTS

| DE | 102007016319 A1 | 10/2008 |
| DE | 102009021521 A1 | 12/2010 |
| DE | 102010022791 A1 | 12/2011 |
| DE | 102011005715 | 9/2012 |
| EP | 2242023 A1 | 10/2010 |

OTHER PUBLICATIONS

Reduction of CT artifacts caused by metallic implants Kalender et al.; Radiology vol. 164, No. 2, Seiten 576-577; Radiology; Magazine; 1987.
T. Hinderling, P. Rüegsegger, M. Anliker, C. Dietschi; Computed tomography reconstruction from hollow projections: an application to in vivo evaluation of artificial hip joints Hinderling et al.; J Comput Assist Tomogr. Feb. 1979;3(1):52-57.; Others; 1979;.
D. Felsenberg, W. Kalender, R. Sokiranski, J. Ebersberger, R. Krämer; Reduktion von Metallartefakten in der Computertomographie: Klinische Erfahrungen und Ergebnisse Electromedica, 56(3), pp. 97-104, 1988; Others; 1988.
A.H. Mahnken et al.; A new algorithm for metal artifact reduction in computed tomography: in vitro and in vivo evaluation after total hip replacement Invest Radiol. Dec. 2003;38(12):769-775; Others; 2003.
B. De Man, J. Nuyts, P. Dupont, G. Marchal, and P. Suetens; Reduction of metal streak artifacts in x-ray computed tomography using a transmission maximum a posteriori algorithm De Man et al.; IEEE Transactions on Nuclear Science, vol. 47, nr. 3, 2000, pp. 977-981; Others; 2000.

(Continued)

Primary Examiner — Atiba O Fitzpatrick

(57) ABSTRACT

A method is provided for supplying a 3D X-ray image data record for a moving object. The said object contains highly X-ray radiation-absorbent material. A correction is made in respect of the highly absorbent material in 2D forward projections obtained from a 3D-X-ray image data record. The forward projections are calculated using 3D motion fields, which are derived from original 2D X-ray image data records.

7 Claims, 1 Drawing Sheet

(56) References Cited

OTHER PUBLICATIONS

Jan Müller and Thorsten M. Buzug; Intersection Line Length Normalization in CT Projection Data Buchreihen Informatik aktuell Buch Bildverarbeitung für die Medizin 2008 Verlag Springer Berlin Heidelberg Part 4, pp. 77-81; Book; 2008.

Esther Meyer et al. Normalized Metal Artifact Reduction (NMAR) in Computed Tomography Nuclear Science Symposium Conference Record (NSS/MIC), 2009 IEEE, pp. 3251-3255 M09-206; Others; 2009.

G. Lauritsch et al.: "3D imaging of myocardial perfusion and coronary tree morphology from a single rotation angiogram", Konferenzbeitrag für SPIE Medical Imaging Conference, Lake Buena Vista (Orlando Area, Florida, USA, 12.-17.2.2011; Others; 2011.

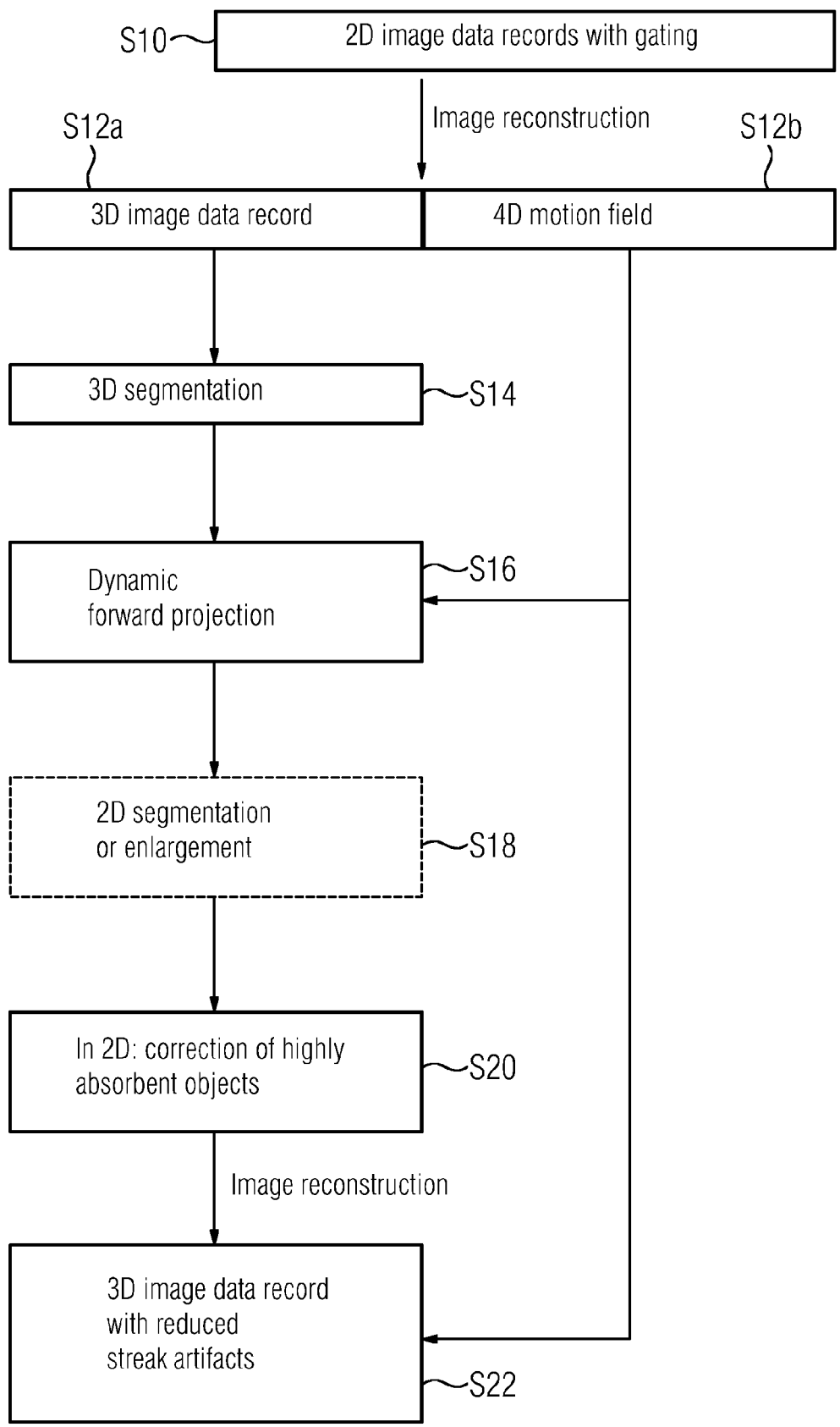

METHOD FOR SUPPLYING A 3D X-RAY IMAGE DATA RECORD FOR A MOVING OBJECT WITH HIGHLY ABSORBENT MATERIAL

CROSS REFERENCE TO RELATED APPLICATIONS

This application claims priority of German application No. 10 2011 017 710.8 filed Apr. 28, 2011, which is incorporated by reference herein in its entirety.

FIELD OF INVENTION

The invention relates to a method for supplying a 3D X-ray image data record for a moving object, which contains highly X-ray radiation-absorbent material.

BACKGROUND OF INVENTION

The present invention is based on the knowledge that such a 3D image data record can be acquired from a number of 2D X-ray image data records, which are acquired with the aid of an X-ray radiation source and an X-ray radiation detector, which are moved one after the other into different rotational positions of a rotation in relation to a rotation axis, to acquire a 2D image data record in each instance. The so-called filtered back projection according to Feldkamp can then be used to calculate a 3D X-ray image data record.

In the present instance a 3D X-ray image data record is to be acquired for a moving object, for example the heart or the coronary arteries. Highly X-ray radiation-absorbent material is to be present here. This may be the metal in a catheter, a pacemaker cable or pacemaker electrodes but the highly X-ray radiation-absorbent material may also be a contrast agent introduced into the coronary arteries.

Two problems currently arise: while the 2D X-ray image data records are being acquired, the object is moving, making the acquisition of a 3D X-ray image data record difficult. Also the highly X-ray radiation-absorbent material produces artifacts in such a 3D X-ray image data record, these occurring in the form of stripes.

A number of designers have concerned themselves with supplying a 3D X-ray image data record for a moving object in recent times. For example EP 2 242 023 A1 deals with a method for reconstructing a three-dimensional final image data record with motion compensation. In this, as the 2D X-ray image data records are being acquired, associated information relating to a phase in the period of movement of the object is also acquired. Such a phase is referred to as a cardiac phase. It is then possible, for example using the method claimed in EP 2 242 023 A1, to calculate a 3D X-ray image data record from the 2D X-ray image data records. So-called motion fields can also be calculated for the individual phase intervals. For example the method for registering the images or back projection of the images of a phase interval to those of a reference phase interval makes it possible to determine which parts of the object are moving. This allows the motion fields to be derived. It is then possible also to derive the 3D X-ray image data record with the aid of all the 2D X-ray image data records from all the information relating to the movements.

A number of people have concerned themselves with the problem of suppressing artifacts, which result for example due to metal in the image object. It is thus known from Kalender et al., "Reduction of CT artefacts caused by metallic implants", Radiology, August 1987, 164, pp. 576 to 577 to segment X-ray images, in other words to generate contours, which isolate regions of differing absorbency from one another. Segmentation takes place here in a 3D back projection. The segmented 3D back projection is then projected forward again. In the forward projection the metallic projection profile is replaced by a linearly interpolating segment in the, at the time of Kalender et al., single-line CT recordings. Later Müller and Buzug, "Intersection line Length Normalization in CT Projection Data" in Bildverarbeitung für die Medizin [Medical image processing] 2008, Springer-Verlag Berlin Heidelberg, proposed length-normalized line integral projection images to improve the interpolation result. Meyer et al., in their article "Normalized Metal Artifact Reduction (NMAR) in computed tomography", in: IEEE Medical Imaging Conference, Record. 2009, Proceedings M09-206, October 2009, Orlando, Fla., then brought the length normalization method into general use.

However the known methods for eliminating metal artifacts always assume that the object is stationary.

SUMMARY OF INVENTION

The object of the present invention is to provide a method for supplying a 3D X-ray image data record for a moving object, which contains highly X-ray radiation-absorbent material.

The object is achieved by a method with the features claimed in the claims. The method thus comprises the following steps:
 a) Acquiring a number of 2D X-ray image data records,
 b) Calculating a motion-compensated 3D X-ray image data record from the 2D X-ray image data records and calculating a motion field for each time point of the images of the 2D X-ray image data record,
 c) Processing the 3D-X-ray image data record so that the contours of the highly absorbent material are emphasized,
 d) Calculating a number of 2D forward projections of the processed 3D X-ray image data record, which correspond to the 2D image data records, using the 3D motion fields,
 e) Processing the 2D forward projections so that the data values in regions predefined by the contours are changed so that the effect of the high level of absorption is reduced (and in particular suppressed), in other words the data values become less extreme,
 f) Calculating a motion-compensated 3D X-ray image data record from the processed 2D forward projections using the 3D motion fields.

The invention succeeds in significantly reducing artifacts due to the highly X-ray radiation-absorbent material, so that the image quality is good when displaying the periodically moving object. This allows quite novel types of examinations to be undertaken, in particular allowing a moving object, such as the heart and the surrounding myocardium, to be imaged reliably and informatively, even when certain metal objects or a contrast agent is/are introduced into the object.

The invention is based primarily on the knowledge that the 3D motion fields not only provide image information themselves but that they can also be used with a 2D forward projection to produce the same situation with the aid of the 2D forward projection as existed when recording an associated 2D X-ray image data record; this allows uncomplicated elimination of the traces of the highly X-ray radiation-absorbent material in the 2D forward projections corresponding to the 2D X-ray image data records.

It is preferable in the known manner in step e) for the data values in the regions enclosed by the contours to be replaced by data values interpolated from the data values in the regions outside the contours. It is thus possible to use known methods. In particular it is irrelevant when processing the 2D forward projections whether or not the object is a moving object.

A segmentation preferably takes place in step c). Segmentation means that a particular data value is assigned to a number of data values, which are associated with a specific interval. In the most extreme instance segmentation is binary, in other words data values relating to highly X-ray radiation-absorbent material are set in a binary manner to "one" and the others are set to "zero".

Segmentation can also take place between the steps d) and e) in respect of the 2D forward projection, in order to determine the contours more precisely there. Similarly enlargement of the region enclosed by the contours, in other words displacement of the contours, can also take place between steps d) and e). It is possible thus to be rather more certain that data values do not relate to the highly X-ray radiation-absorbent material in a region outside the contours.

BRIEF DESCRIPTION OF THE DRAWINGS

A preferred embodiment of the invention is described in more detail below with reference to the drawing, in which the single FIGURE is a flow diagram describing this particular embodiment of the inventive method.

DETAILED DESCRIPTION OF INVENTION

The method is intended to serve for example to acquire images of a heart with the surrounding myocardium, even when a catheter containing metal is inserted.

The method starts in step S10 by acquiring a number of 2D X-ray image data records by moving an X-ray radiation source with an X-ray radiation detector one after the other into different rotational positions in relation to a rotation axis. Image reconstruction then takes place to acquire an image data record according to step S12a and at the same time a 4D motion field in step S12b. The image reconstruction can take place for example using the method from EP 2 242 023 A1. The 3D image data record is based on all the 2D image data records. The 4D motion field is simply a sequence of 3D motion fields ordered according to the recording time of the 2D X-ray images.

A 3D segmentation can then take place in step S14 based on the 3D image data record. During segmentation the individual gray scale values for volume elements forming the 3D image data record are allocated a new gray scale value; in this process the new gray scale value is determined by the interval in which the gray scale value occurs out of a number of gray scale values. 3D segmentation therefore emphasizes specific gray scale value regions in particular, producing a contour. 3D segmentation primarily takes place here in that the regions relating to metal (specifically the metal of the catheter) are emphasized particularly. In step S16 a dynamic forward projection takes place; such a forward projection is calculated for each of the 2D image data records acquired in step S10, using the 4D motion field according to S12b. This allows the 2D-image data records to be back calculated again from the 3D image data record S12a, with the intermediate step S14 of segmentation allowing the metal to be emphasized particularly in the new 2D image data records acquired as a result of step S16. Step S16 can be followed by a step S18 but this is not necessarily the case: step S18 requires segmentation to take place again in the 2D forward projections. Optionally the region produced in the 2D forward projection image from the 3D segmentation, which was projected forward, can also be enlarged, in other words the contours can be displaced.

After step S18 or optionally, if this is omitted, after step S16, in step S20 the correction of highly absorbent objects, in other words of the metal, takes place in the 2D forward projections, with an interpolation being performed according to one of the methods described in the introduction or another method. This correction involves data values (gray scale values) extending into the extreme being replaced by data values appropriate for the surroundings.

Once a plurality of 2D forward projections is available having been corrected in respect of the highly absorbent objects, an image reconstruction takes place, so that according to S22 a 3D image data record is acquired, which now has reduced streak artifacts. The 4D motion field S12b is used during image reconstruction, so that the image reconstruction calculation between steps S20 and S22 is simpler than between steps S10 and S12a or S12b.

The 3D image data record with the reduced streak artifacts can be used, together with the still valid 4D motion field S12b, to supply any images of the moving object, specifically the heart. The catheter is visible where it contains no metal.

Using the 4D motion field it is possible in particular to define a time sequence, in other words a sort of film is shown, of how the image data evolves over time.

The invention provides new possibilities for displaying moving objects which contain highly X-ray radiation-absorbent material.

The invention claimed is:

1. A method for supplying a 3D X-ray image data record for a moving object comprising highly X-ray radiation-absorbent material, comprising:
    acquiring a plurality of 2D X-ray image data records of the moving object;
    calculating a 3D X-ray image data record from the 2D X-ray image data records;
    calculating a plurality of motion fields corresponding to the 2D X-ray image data records respectively;
    processing the 3D-X-ray image data record for emphasizing a contour of the highly absorbent material;
    calculating a plurality of 2D forward projections from the processed 3D X-ray image data record corresponding to the 2D image data records using the motion fields respectively;
    processing the 2D forward projections for changing data values in regions enclosed by the contour to reduce an effect of a high level absorption; and
    calculating a further 3D X-ray image data record from the processed 2D forward projections using the motion fields.

2. The method as claimed in claim 1, wherein the data values in the regions enclosed by the contour are replaced by data values interpolated from data values in regions outside the contour.

3. The method as claimed in claim 1, wherein the 3D-X-ray image data record is segmented.

4. The method as claimed in claim 1, wherein the 2D forward projections are segmented before processing.

5. The method as claimed in claim 1, wherein the regions enclosed by the contour are enlarged in the 2D forward projections before processing.

6. The method as claimed in claim 1, wherein information about a motion state of the moving object is recorded in addition to the 2D-X-ray image data records.

7. The method as claimed in claim 6, wherein the information about the motion state of the moving object is an electrocardiogram.

\* \* \* \* \*